(12) United States Patent
Dolbier, Jr. et al.

(10) Patent No.: US 6,770,789 B2
(45) Date of Patent: Aug. 3, 2004

(54) PROCESS FOR TRIFLUOROMETHYLATION OF SULFATES

(75) Inventors: William R. Dolbier, Jr., Gainesville, FL (US); Naoto Takechi, Gunma (JP)

(73) Assignee: University of Florida Research Foundation, Gainesville, FL (US)

( * ) Notice: Subject to any disclaimer, the term of this patent is extended or adjusted under 35 U.S.C. 154(b) by 0 days.

(21) Appl. No.: 10/387,978

(22) Filed: Mar. 13, 2003

(65) Prior Publication Data

US 2003/0199715 A1 Oct. 23, 2003

Related U.S. Application Data

(60) Provisional application No. 60/364,830, filed on Mar. 13, 2002.

(51) Int. Cl.[7] .......................... C07C 31/34; C07C 29/00; C07C 31/00; C07C 31/02; C07C 33/00
(52) U.S. Cl. ...................... 568/842; 568/840; 568/841; 570/140; 570/162
(58) Field of Search ................................ 568/842, 840, 568/841; 570/140, 162

(56) References Cited

U.S. PATENT DOCUMENTS 5,565,689 A 10/1996 Clavel et al.

OTHER PUBLICATIONS

Aïc-Mohand, S. et al. "Nucleophilic Trifluoromethylation Using Trifluoromethyl Iodine. A New and Simple Alternative for the Trifluoromathylation of Aldehydes and Ketones" *Organic Letters* 2001, vol. 3, No. 26, pp. 4271–4273.

Billard, T. et al. "New Stable Reagents for Nucleophilic Trifluoromethylation. 3. Trifluoromethylation of Nonenolizable Carbonyl Compounds with a Stable Piperazino Hemiaminal of Trifluoroacetaldehyde" *Eur. J. Org. Chem.* 2001, pp. 1467–1471.

Burkholder, C.R. et al. "Tetrakis (dimethylamino) ethylene as a Useful Reductant of Some Bromodifluoromethyl Heterocycles. Application to the Synthesis of New gem–Diffuorinated Heteroarylated Comnpounds" *J. Org. Chem.* 1998, vol. 63, pp. 5385–5394.

Burkholder, C.R. et al. "Systhesis and reactivity of halogeno–difluoromethyl aromatics and heterocycles Application to the synthesis of gem–difluorinated bioactive compounds" *J. Fluorine Chem.* 2001, vol. 109, pp. 39–48.

Kitazume, T. et al., "Ultrasound–Promoted Selective Perfluoroalkylation on the Desired Position of Organic Molecules" *J. Am. Chem. Soc.* 1995, vol. 107, pp. 5186–5191.

Krishnamurti, R. et al., "Preparation of Trifluoromethyl and Other Perfluoroalkyl Compounds with (Perfluoralkyl) trimethylsilanes" *J. Org. Chem* 1991, vol. 56, pp. 984–989.

Large, S. et al. "Nucleophilic trifluoromethylation of carbonyl compounds and disulfides with trifluoromethane an silicon–containing bases" *J. Org. Chem.* 2000, vol. 65, pp. 8848–8856.

Pawelke, G., "Tetrakis (dimethylamino) ethylene/trifluoro iodomethane, a Specific Novel Trifluoromethylating Agent" *Journal of Fluorine Chemistry* 1989, vol. 42, No. 3, pp. 429–433.

Pawelke, G.J. "Reaction of Tetrakis (dimethylamino) Ethylene with $CF_2Br_2$ in the presence of secondary amines, formation of N–Trifluoromethyl–Dialkylamines" *Fluorine Chem.* 1991, vol. 52, p. 229.

Singh, R.P, et al. "Nucleophilic Trifluoromethylation Reactions of Organic Compounds with (Trifluoromethyl)trimethylsilane" *Tetrahedron* 2000, vol. 56, pp. 7613–7632.

Takechi, N. et al. "Novel Nucleophilic Trifluoromethylation of Vicinal Diol Cyclic Sulfates" *Organic Letters* 2002, vol. 4, No. 26, pp. 4671–4672.

Vanhessche, et al. "Catalytic Asymmetric Synthesis of Halogenated Chiral Synthons" *A European Journal* 1997, vol. 3, No. 4, pp. 517–522.

Prakash and Yudin, "Perfluoroalkylation with Organosilicon Reagents" *Chem. Rev.* 1997, vol. 97, pp. 757–786.

*Primary Examiner*—Elvis O. Price
(74) *Attorney, Agent, or Firm*—Saliwanchik, Lloyd & Saliwanchik (57) ABSTRACT

The subject invention relates to a process for the trifluoromethylation of sulfates, including cyclic and acyclic sulfates. The subject invention further pertains to the compounds produced by the trifluoromethylation of sulfates.

15 Claims, 5 Drawing Sheets

PROCESS FOR TRIFLUOROMETHYLATION OF SULFATES

CROSS-REFERENCE TO RELATED APPLICATION(S)

This application claims the benefit of U.S. Provisional Application No. 60/364,830, filed Mar. 13, 2002.

The subject invention was made with government support under a research project supported by National Science Foundation Grant No. NSF-CHE-9982587.

BACKGROUND OF THE INVENTION

Compounds containing the trifluoromethyl group are of great interest in the pharmaceutical and agrochemical industry. Among the numerous methods for incorporation of the trifluoromethyl group into organic compounds (McClinton, M. A. et al. *Tetrahedron*, 1992, 48:6555–6666), one of the most useful involves the use of reagents that effectively generate the unstable $CF_3^-$ anion as an in situ species for the purpose of nucleophilic trifluoromethylation of electrophilic substrates such as aldehydes and ketones. Because of the limited number of such reagents and because of specific limitations that pertain to each, there remains considerable interest in the development of new trifluoromethyl anion reagents that might offer an experimental or cost advantage.

Currently, there are two major trifluoromethyl anion methodologies that receive most of the attention from synthetic chemists around the world. Because of its diversity of applicability, deriving from extensive recent work by several research groups (Prakash, G. K. S. et al. *Chem. Rev.*, 1997, 97:757–786; Singh, R. P. et al. *Tetrahedron*, 2000, 56:7613–7632; Prakash, G. K. S. et al. *Chem. Rev.*, 1997, 97:757–786; Singh, R. P. et al. *Tetrahedron*, 2000, 56:7613–7632), (trifluoromethyl)-trimethylsilane ($Me_3SiCF_3$) is generally considered to be the most effective reagent of this type, but recent advances using trifluoroacetaldehyde hemiaminals and their derivatives as trifluoromethylating reagents in reactions with nonenolizable aldehydes and ketones have also sparked considerable interest (Large, S. et al. *J. Org. Chem.*, 2000, 65:8848–8856, Billard, T. et al *Eur. J. Org. Chem.*, 2001, pp. 1467–1471).

Trifluoromethyl iodide has previously been used for the purpose of nucleophilic trifluoromethylation of carbonyl compounds, via its derived organozinc reagent. However, the required use of ultrasound for these reactions seems to have limited their use by synthetic chemists (Kitazume, T. et al. *J. Am. Chem. Soc.*, 1985, 107:5186–5191; Francese, C. et al. *J. Chem. Soc., Chem Commun.*, 1987, pp. 642–643).

Beginning in 1998, it was demonstrated that tetrakis (dimethylamino)ethylene (TDAE) could be used as an effective reductant to generate synthetically competent nucleophilic heterocyclic difluoromethyl anions from chloro- and bromodifluoromethyl precursors (Burkholder, C. R. et al. *J. Org. Chem.*, 1998, 63:5385–5394; Burkholder, C. R. et al. *J. Fluorine Chem.*, 2001, 109:39–48). It was demonstrated that the combination of $CF_3I$ and TDAE could be used to prepare $CF_3TMS$ from TMSCl (Pawelke, G. *J. Fluorine Chem.*, 1991, 52:229). A method for the nucleophilic trifluoromethylation of aldehydes and ketones, based on photo-induced reduction of trifluoromethyl iodide by TDAE has also recently been demonstrated (Ait-Mohand, S. et al. *Organic Letters*, 2001, 3(26):4271–4273).

Despite their varying degrees of success with other organic compounds, none of the known trifluoromethyl anion methodologies have been utilized to achieve trifluoromethylation of sulfates.

BRIEF SUMMARY OF THE INVENTION

The subject invention provides materials and methods for the trifluoromethylation of sulfates. In a preferred embodiment, the processes of the subject invention comprise reacting a trifluoromethylating reagent with a sulfate to synthesize a trifluoromethylated carbinol.

Cyclic sulfates or acyclic sulfates can be trifluoromethylated according to the process of the subject invention. For example, cyclic sulfates, such as a 1,2-cyclic sulfate or 1,3-cyclic sulfate, can be utilized to synthesize a trifluoromethylated carbinol, such as 3,3,3-trifluoroethycarbinol or 4,4,4-trifluoropropylcarbinol, respectively.

In view of the ready availability of chiral, optically-pure 1,2-diols, which are precursors of cyclic sulfates, the process of the subject invention advantageously permits ring-opening trifluoromethylation of cyclic sulfates, and efficient synthesis of chiral, optically-pure trifluoromethylated carbinols, such as 3,3,3-trifluoroethylcarbinols.

In specific embodiments, the trifluoromethylating reagent utilized to carry out the process of the subject invention can be selected from the group consisting of: (i) trifluoromethyl iodide ($CF_3I$) and tetrakis(dimethylamino)ethylene (TDAE); (ii) $HCF_3$/dimethylformamide (DMF) with $N(SiMe_3)_3/Me_4NF$; (iii) a hemiaminal with a strong base, such as potassium tert-butoxide (tBuOK); and (iv) trifluoromethyltrimethyl silane ($CF_3Si(CH_3)_3$).

The processes of the present invention allow a unique placement of the trifluoromethyl group relative to the alcohol function, and allows it to be done in a chiral manner.

The present invention also pertains to compounds, such as chiral compounds, produced using the processes of the subject invention. The compounds of the subject invention comprise trifluoromethylated carbinols.

DETAILED DISCLOSURE OF THE INVENTION

The subject invention relates to processes for the trifluoromethylation of cyclic or acyclic sulfates. In a preferred embodiment of the subject invention, the process comprises the step of reacting a trifluoromethylating reagent with a sulfate, thereby producing a carbinol.

Advantageously, the trifluoromethylating process of the subject invention can be carried out in a highly stereospecific and regioselective manner, using readily available starting materials.

In specific examples exemplified herein, the trifluoromethylating reagent utilized to carry out the process of the subject invention can be selected from the group consisting of: (i) trifluoromethyl iodide ($CF_3I$) and tetrakis(dimethylamino)ethylene (TDAE); (ii) $HCF_3$/dimethylformamide (DMF) with $N(SiMe_3)_3/Me_4NF$; (iii) a hemiaminal with a strong base, such as potassium tert-butoxide (tBuOK); and (iv) trifluoromethyltrimethyl silane ($CF_3Si(CH_3)_3$).

The compounds utilized as trifluoromethylating reagents in the process of the subject invention have been described previously (Ait-Mohand, S. et al. *Organic Letters* [2001] 3(26):4271–4273; Large, S. et al., *J. Org. Chem.* [2000] 65:8848–8856; Billard, T. et al,. *J. Org. Chem.*; Krishnamurti, R. et al., *J. Org. Chem.* [1991] 56:984–989).

Any of a variety of cyclic or acyclic sulfates can be trifluoromethylated using the process of the subject invention. Cyclic sulfates that can be trifluoromethylated using the process of the subject invention can comprise, for example, a ring with five members, six members, seven members, eight members, and so forth.

Reaction of the trifluoromethylating reagent with a sulfate, according to the process of the subject invention, can be carried out by mixing, or otherwise introducing the reagent with the sulfate, or vice-versa. Reactants can be added in any particular order desired. Preferably, the reaction of the trifluoromethylating reagent with the sulfate is carried out in the presence of a solvent. To minimize thermal decomposition, the reactants can be introduced at an initial temperature from about −40° C. to about 20° C. Preferably, the initial reaction temperature is about −20° C. The reaction takes place as the reactants warm to room temperature. This warming period ranges from about four hours to about eight hours. The warming step can be carried out in the presence or absence of irradiation.

In addition to reacting a trifluoromethylating reagent with a sulfate, the process of the subject invention can further comprise one or more of the steps of filtering the solution, washing any solid (such as with ether), hydrolyzing the resulting solution (such as with $H_2SO_4$), and separating the resulting mixture (such as with ether). The hydrolysis step is preferably carried out for about one hour to eight hours. The resultant carbinol can be separated from the reaction medium by known organic chemistry techniques, such as distillation or extraction.

Figure 1:
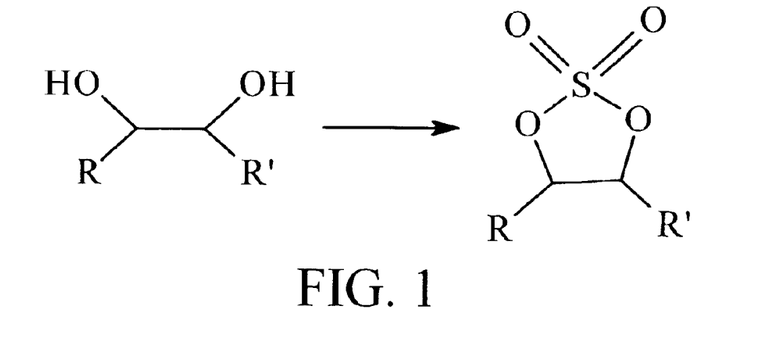
FIG. 1 shows the conversion of a diol with adjacent —OH functional groups to its corresponding cyclic sulfate.
Figure 2:
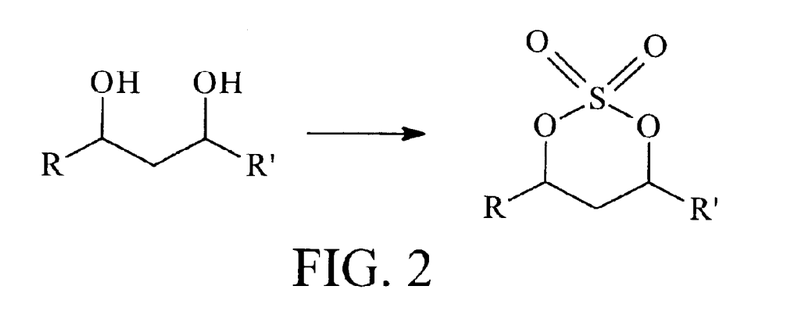
FIG. 2 shows the conversion of a diol with two —OH functional groups separated by a carbon to its corresponding cyclic sulfate.

FIGS. 1 and 2 show examples of reaction schemes with mono-substituted and di-substituted diols that can be utilized to produce the sulfates for the process of the subject invention. Advantageously, diols, a precursor compound for cyclic sulfates, is a readily available reactant. Diols utilized to produce the sulfates can, optionally, be chiral (optically active).

Figure 3:
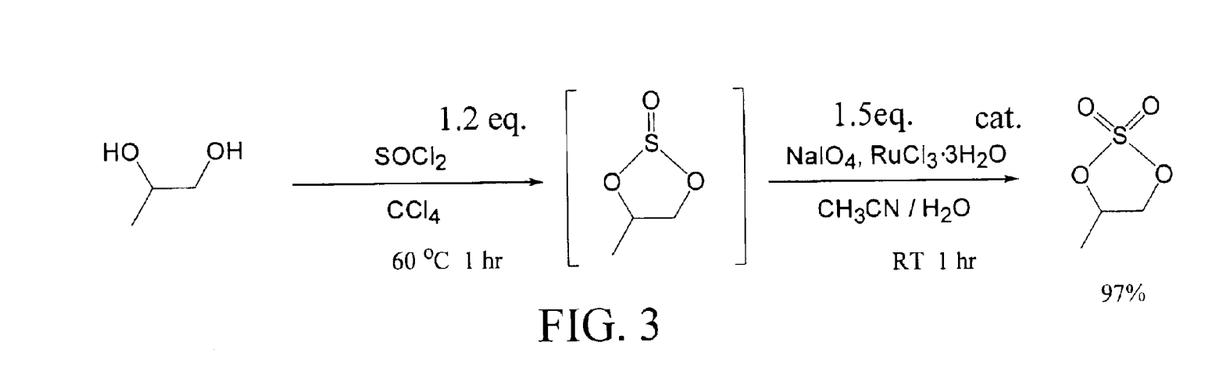
FIG. 3 shows a reaction scheme for the production of cyclic sulfates from 1,2-propylenediol, with reaction conditions and yield.

In one embodiment, a diol can be reacted with $SOCl_2$ and $NaIO_4$ in the presence of a catalyst to produce a cyclic sulfate useful according to the subject invention. FIG. 3 shows a reaction scheme for the production of cyclic sulfates from 1,2-propylenediol, with reaction conditions and yield.

Figure 8:
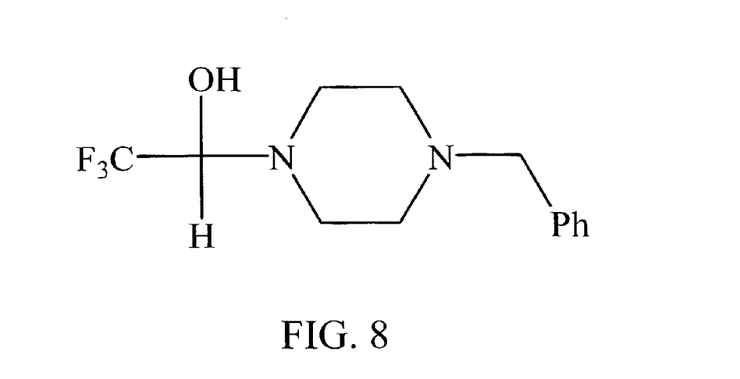
FIG. 8 shows a hemiaminal that can be utilized with tBuOK to trifluoromethylate sulfates using the process of the subject invention.
Figure 9:
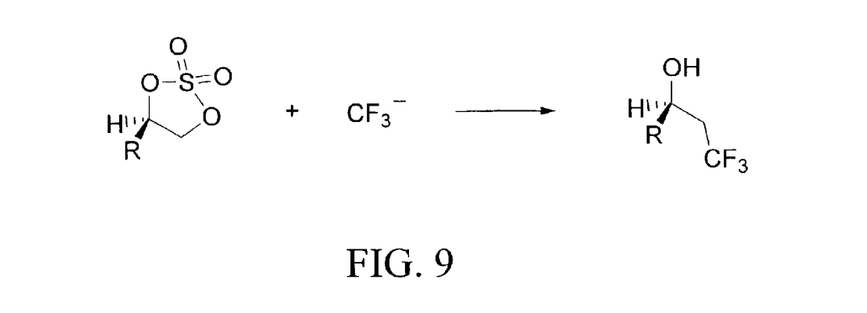
FIG. 9 shows an example of a reaction scheme for the stereospecific trifluoromethylation of a cyclic sulfate using the process of the subject invention.
Figure 10:
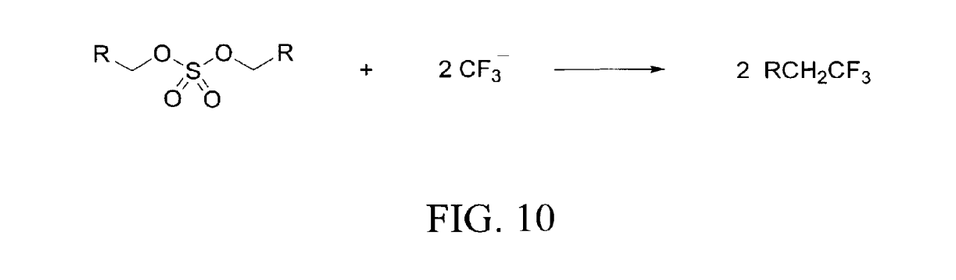
FIG. 10 shows an example of a reaction scheme for the trifluoromethylation of an acyclic sulfate using the process of the subject invention.

FIGS. 4–7 show examples of reaction schemes for the trifluoromethylation of sulfates according to the process of the subject invention. FIG. 8 shows a hemiaminal that can be utilized with tBuOK as a trifluoromethylating agent according to the process of the subject invention. FIG. 9 shows an example of a reaction scheme for the stereospecific trifluoromethylation of a cyclic sulfate, according to the process of the subject invention. FIG. 10 shows an example of a reaction scheme for the trifluoromethylation of an acyclic sulfate, according to the process of the subject invention.

It would be understood by those of ordinary skill in the art that the diols, sulfates, and carbinols depicted in the reaction schemes shown in the Figures can be optionally substituted with R or R' at any available position or positions. For example, carbons at the #1 and #2 positions of the diols, sulfates, and carbinols, can be substituted with R or R'.

In each of the Figures, R and R' can each be an appropriately functionalized group, such as an ester, ether, or haloalkyl. R and R' can each be hydrogen, alkyl, alkenyl, alkynyl, or alkoxy. R and R' can each be a cyclic group, such as cycloalkyl, cycloalkenyl, heterocycloalkyl, heterocycloakenyl, aryl, or heteroaryl. R and R' can be the same or different. In specific embodiments, R and R' can be selected from the group consisting of n-$C_3H_7$, I-$C_3H_7$, 3-chloropropyl-, $C_6H_5$, 3-pyridyl, and 2-thiyl. In one embodiment, R and R' are each not an alcohol group, an amino group, or a carboxylic acid group.

As used in the specification, the term "alkyl" refers to a straight or branched chain alkyl moiety. In one embodiment, the alkyl moiety is $C_{1-8}$ alkyl, which refers to an alkyl moiety having from one to eight carbon atoms, including for example, methyl, ethyl, propyl, isopropyl, butyl, tert-butyl, pentyl, hexyl, octyl, and the like.

The term "alkenyl" refers to a straight or branched chain alkyl moiety having in addition one or more carbon-carbon double bonds, of either E or Z stereochemistry where applicable. In one embodiment, the alkenyl moiety is $C_{2-6}$ alkenyl, which refers to an alkenyl moiety having two to six carbon atoms. This term would include, for example, vinyl, 1-propenyl, 1- and 2-butenyl, 2-methyl-2-propenyl, and the like.

The term "alkynyl" refers to a straight or branched chain alkyl moiety having in addition one or more carbon-carbon triple bonds. In one embodiment, the alkynyl moiety is $C_{2-6}$ alkynyl, which refers to an alkynyl moiety having two to six carbon atoms. This term would include, for example, ethynyl, 1-propynyl, 1- and 2-butynyl, 1-methyl-2-butynyl, and the like.

The term "alkoxy" refers to an alkyl-O-group, in which the alky group is as previously described.

The term "halogen" refers to fluorine, chlorine, bromine, or iodine.

The term "cycloalkenyl" refers to an alicyclic moiety having from three to six carbon atoms and having in addition one double bond. This term includes, for example, cyclopentenyl and cyclohexenyl.

The term "heterocycloalkyl" refers to a saturated heterocyclic moiety having from two to six carbon atoms and one or more heteroatom from the group N, O, S (or oxidized versions thereof) which may be optionally benzofused at any available position. This includes for example azetidinyl, pyrrolidinyl, tetrahydrofuranyl, piperidinyl, benzodioxole and the like.

The term "heterocycloalkenyl" refers to an alicyclic moiety having from three to six carbon atoms and one or more heteroatoms from the group N, O, S and having in addition one double bond. This term includes, for example, dihydropyranyl.

The term "aryl" refers to an aromatic carbocyclic ring, optionally substituted with, or fused with, an aryl group. This term includes, for example phenyl or naphthyl.

The term "heteroaryl" refers to aromatic ring systems of five to ten atoms of which at least one atom is selected from O, N, and S, and optionally substituted with an aryl group substituent. This term includes for example furanyl, thiophenyl, pyridyl, indolyl, quinolyl and the like.

It will be appreciated that the reactants and products of the process of the subject invention can contain one or more asymmetrically substituted carbon atoms (a chiral center). The presence of one or more of these asymmetric centers can give rise to stereoisomers, and in each case the invention is to be understood to extend to all such stereoisomers, including entantiomers and diastereomers, and mixtures including racemic mixtures thereof.

The present invention also pertains to compounds produced using the process of the subject invention. A variety of trifluoromethyl-containing carbinols can be produced using the process of the subject invention, including chiral carbinols. The carbinols produced using the process of the subject invention can have a trifluoromethyl group attached to a carbon adjacent to the carbon from which the —OH of the carbinol is attached. The carbinols produced using the process of the present invention can be utilized in a variety of compounds and chemical processes, such as in pharmaceutical and agrochemical products.

Following are examples which illustrate procedures for practicing the invention. These examples should not be construed as limiting. All percentages are by weight and all solvent mixture proportions are by volume unless otherwise noted.

EXAMPLE 1

Trifluoromethylation of Cyclic Sulfates

Figure 4:
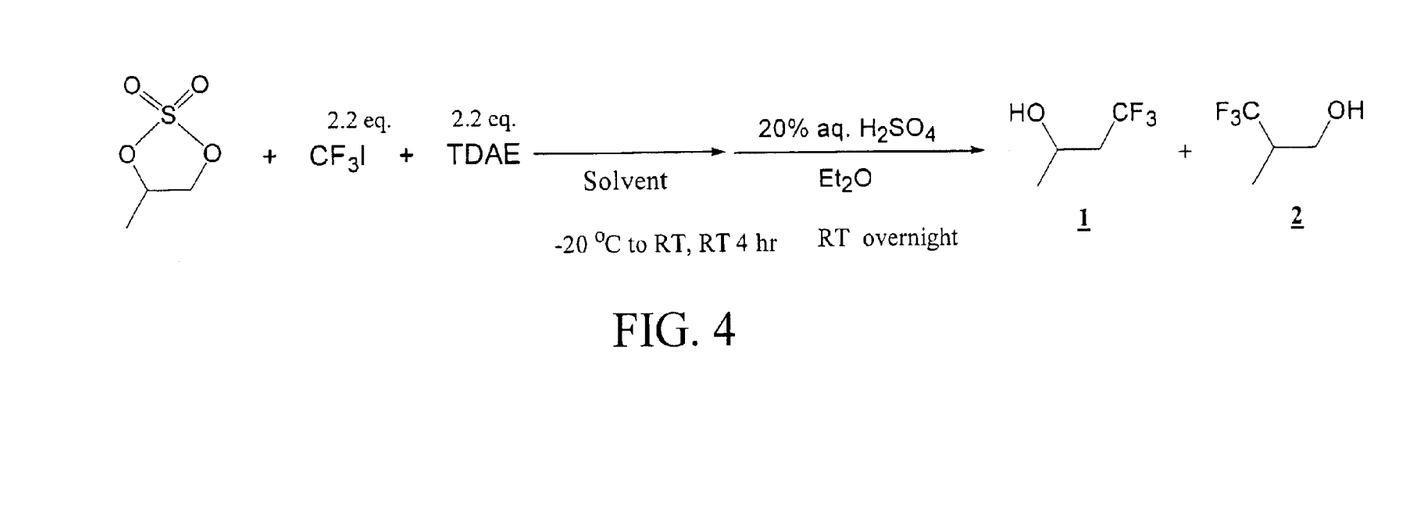
FIG. 4 shows a reaction scheme for the trifluoromethylation process of the subject invention, wherein $CF_3I$ and TDAE are used as the trifluoromethylation reagent.

Following the reaction scheme shown in FIG. 4, cyclic sulfates were trifluoromethylated in the presence of various solvents, including dimethylformamide (DMF), dimethoxyethane (DME), tetrahydrofuran (THF), dichloroethane ($CH_2Cl_2$), and diethyl ether ($Et_2O$). The percentage yield of each carbinol (products 1 and 2) obtained with the solvent utilized is shown in Table 1, wherein product 1 is the preferred carbinol.

TABLE 1

| Entry | Solvent | Yield (%) | |
|---|---|---|---|
| | | 1 | 2 |
| 1 | DMF | 8 | N.D. |
| 2 | DME | 43 | <1 |
| 3 | THF | 55 | 1 |
| 4 | $CH_2Cl_2$ | 10 | N.D. |
| 5 | $Et_2O$ | 23 | trace |

Figure 5:
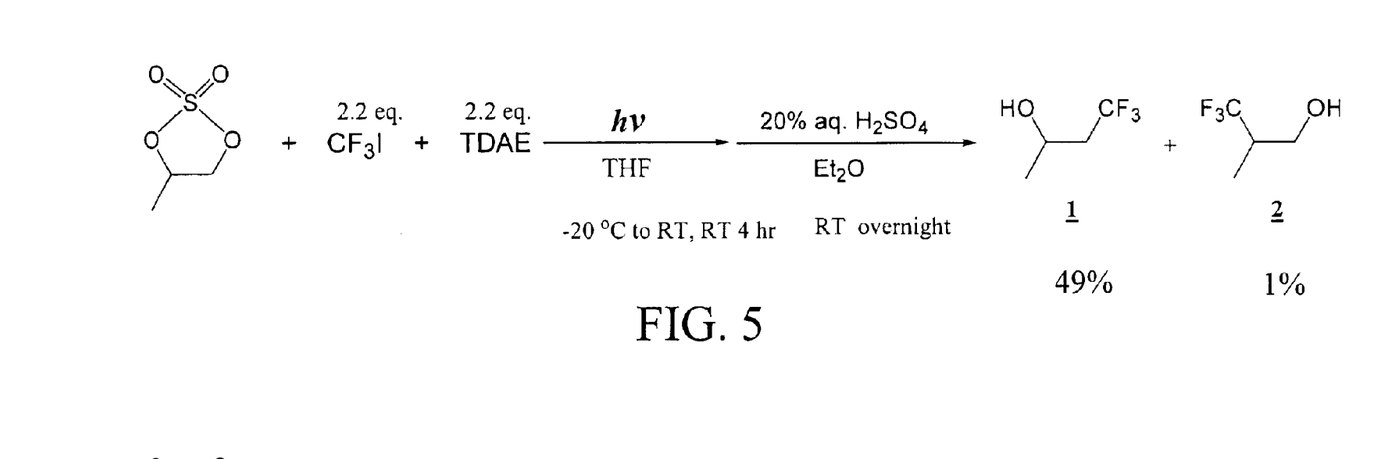
FIG. 5 shows a reaction scheme for the trifluoromethylation process of the subject invention, wherein $CF_3I$ and TDAE were used as the trifluoromethylation reagent and tetrahydrofuran (THF) was utilized as a solvent under irradiation by a sun lamp, and the mixture was warmed to room temperature for four hours.
Figure 6:
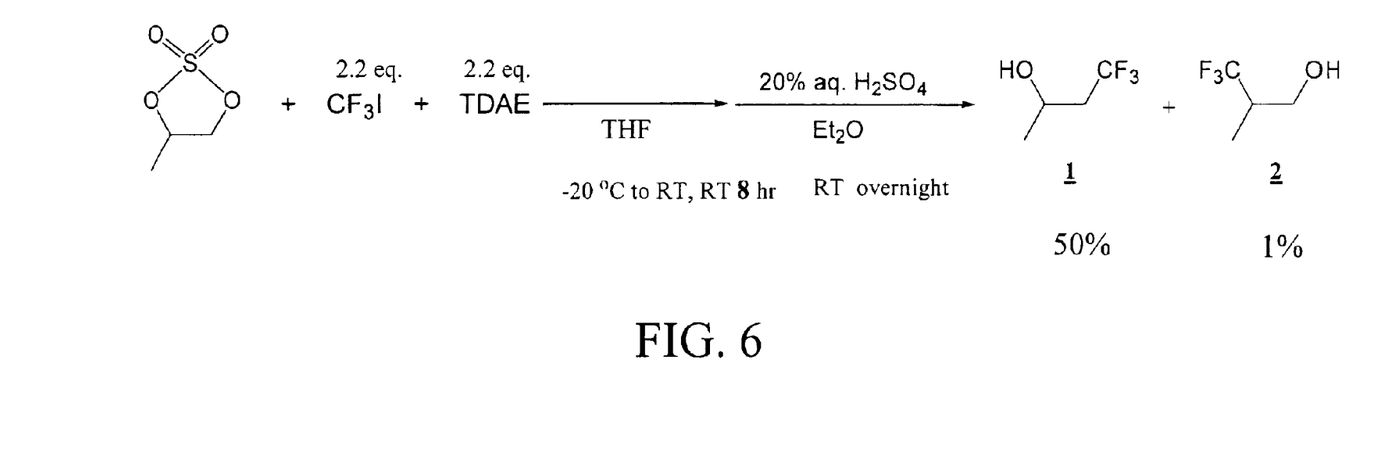
FIG. 6 shows a reaction scheme for the trifluormethylation process of the subject invention, wherein $CF_3I$ and TDAE were used as the trifluoromethylation reagent and THF was utilized as a solvent in the absence of irradiating conditions, and the mixture was warmed to room temperature over eight hours.
Figure 7:
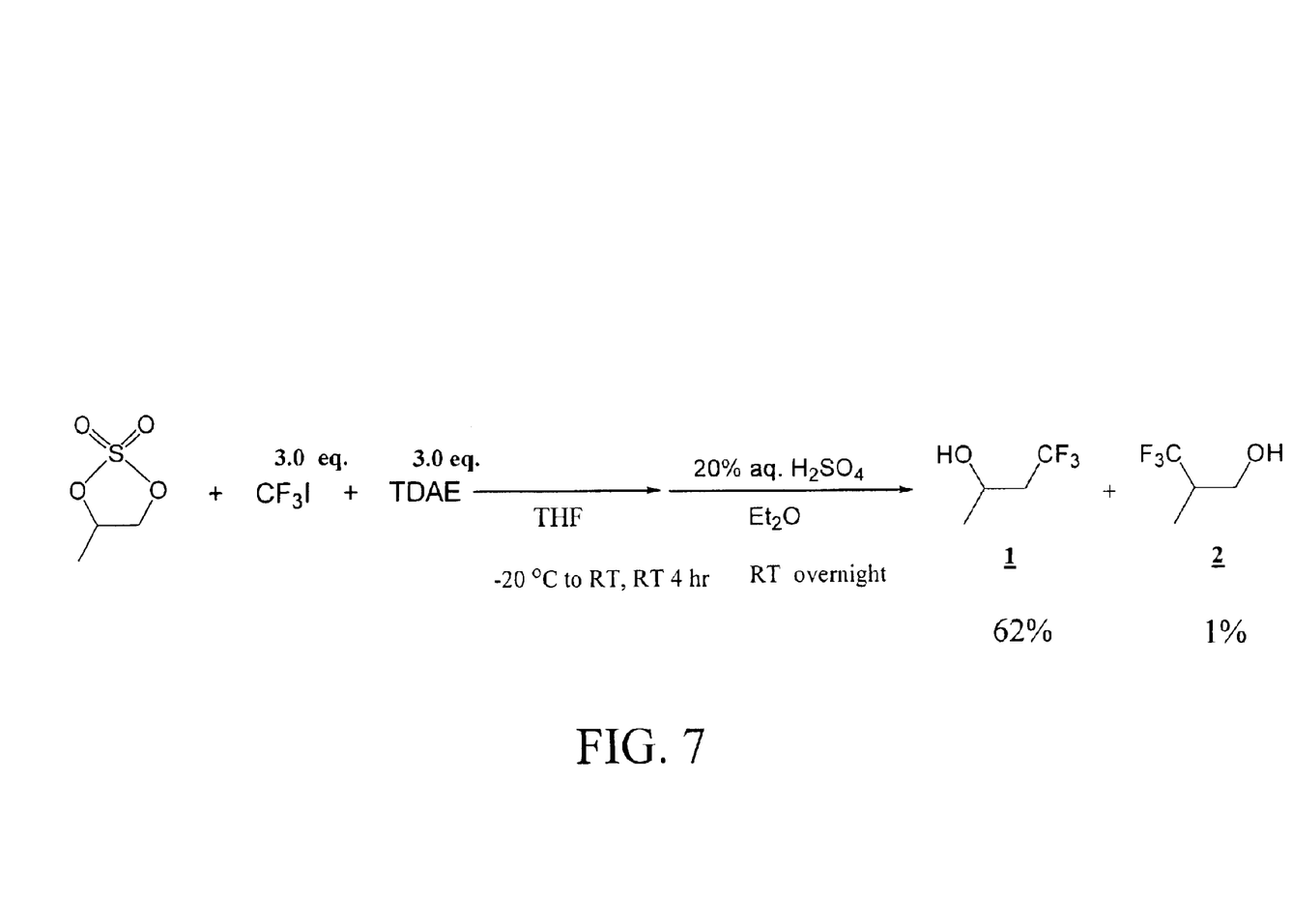
FIG. 7 shows a reaction scheme for the trifluoromethylation process of the subject invention, wherein $CF_3I$ and TDAE were used as the trifluoromethylation reagent and THF was utilized as a solvent in the absence of irradiating conditions, and the mixture was warmed to room temperature over four hours.

FIGS. 5–7 show reaction schemes carried out with resulting percentage yields of carbinols, using various solvents, and $CF_3I$ and TDAE as a trifluoromethylation reagent. The process of the subject invention results in very good product selectivity and yield.

EXAMPLE 2

Trifluoromethylation of Acyclic Sulfates

Following the general reaction scheme shown in FIG. 10, acyclic sulfates can be trifluoromethylated according to the process of the subject invention. The reaction of the acyclic sulfate with the trifluoromethylating reagent can be carried out as described above with respect to cyclic sulfates. The reaction can be carried out in the presence of one or more of a variety of solvents, such as dimethylformamide (DMF), dimethoxyethane (DME), tetrahydrofuran (THF), dichloroethane ($CH_2Cl_2$), or diethyl ether ($Et_2O$).

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A process for synthesizing a trifluoromethylated carbinol wherein the process comprises mixing a trifluoromethylating reagent and a sulfate at a temperature below room temperature to form a first solution, and then warming said first solution to room temperature.

2. The process, according to claim 1, wherein the initial mixing takes place at a temperature between about −40° C. to about 20° C.

3. The process, according to claim 2, wherein the initial mixing temperature is around −20° C.

4. The process, according to claim 1, wherein said warming step continues for about four hours to about eight hours.

5. The process, according to claim 1, further comprising irradiating the mixture during said warming step.

6. The process, according to claim 1, wherein said sulfate is a cyclic sulfate.

7. The process, according to claim 1, wherein said sulfate is acyclic.

8. The process, according to claim 1, wherein the reaction takes place in a solvent that comprises a compound selected from the group consisting of dimethylformamide, dimethoxyethane, tetrahydrofuran, dichloroethane, and diethyl ether.

9. The process, according to claim 1, wherein said trifluoromethylating reagent is selected from the group consisting of: (i) trifluoromethyl iodide ($CF_3I$) and tetrakis (dimethylamino)ethylene (TDAE); (ii) $HCF_3$/dimethylformamide (DMF) with $N(SiMe_3)_3/Me_4NF$; (iii) a hemiaminal with a strong base, such as potassium tert-butoxide (tBuOK); and (iv) trifluoromethyltrimethyl silane $(CF_3Si(CH_3)_3)$.

10. The process, according to claim 9, wherein said trifluoromethylating reagent is trifluoromethyl iodide ($CF_3I$) and tetrakis(dimethylamino)ethylene (TDAE).

11. The process, according to claim 9, wherein said trifluoromethylating reagent is $HCF_3$/dimethylformamide (DMF) with $N(SiMe_3)_3/Me_4NF$.

12. The process, according to claim 9, wherein said trifluoromethylating reagent is a hemiaminal with a strong base, such as potassium tert-butoxide (tBuOK).

13. The process, according to claim 9, wherein said trifluoromethylating reagent is trifluoromethyltrimethyl silane $(CF_3Si(CH_3)_3)$.

14. The process, according to claim 1, used to produce 3,3,3-trifluoro-2-methyl-1-propanol.

15. The process, according to claim 1, used to produce 4,4,4-trifluoro-2-butanol.

* * * * *

UNITED STATES PATENT AND TRADEMARK OFFICE
CERTIFICATE OF CORRECTION

PATENT NO. : 6,770,789 B2  Page 1 of 1
APPLICATION NO. : 10/387978
DATED : August 3, 2004
INVENTOR(S) : William R. Dolbier and Naoto Takechi It is certified that error appears in the above-identified patent and that said Letters Patent is hereby corrected as shown below:

Column 1,
Lines 8-10, "The subject invention was made with government support under a research project supported by National Science Foundation Grant No. NSF-CHE-9982587."

should read

--The subject invention was made with government support under a research project supported by National Science Foundation Grant No. NSF-CHE-9982587. The government has certain rights in the invention.--

Signed and Sealed this

Seventh Day of September, 2010

David J. Kappos
*Director of the United States Patent and Trademark Office*